(12) United States Patent
Winniford et al.

(10) Patent No.: US 9,095,792 B2
(45) Date of Patent: Aug. 4, 2015

(54) CHROMATOGRAPHY OF POLYOLEFIN POLYMERS

(75) Inventors: William L. Winniford, Lake Jackson, TX (US); Rongjuan Cong, Lake Jackson, TX (US); Theodore M. Stokich, Jr., Midland, MI (US); Randy J. Pell, Midland, MI (US); Matthew D. Miller, Lake Jackson, TX (US); Abhishek Roy, Edina, MN (US); Freddy Van Damme, Bruges (BE); Alexander W. Degroot, Sugar Land, TX (US); John W. Lyons, Midland, MI (US); David M. Meunier, Midland, MI (US)

(73) Assignee: Dow Global Technologies LLC, Midland, MI (US)

(*) Notice: Subject to any disclaimer, the term of this patent is extended or adjusted under 35 U.S.C. 154(b) by 400 days.

(21) Appl. No.: 13/512,387

(22) PCT Filed: Dec. 21, 2010

(86) PCT No.: PCT/US2010/061526
§ 371 (c)(1),
(2), (4) Date: May 29, 2012

(87) PCT Pub. No.: WO2011/084786
PCT Pub. Date: Jul. 14, 2011

(65) Prior Publication Data
US 2012/0227469 A1 Sep. 13, 2012

(51) Int. Cl.
*C08J 3/00* (2006.01)
*B01D 15/16* (2006.01)
*B01D 15/18* (2006.01)
*B01J 20/24* (2006.01)
*G01N 30/34* (2006.01)
*C08F 6/00* (2006.01)
*G01N 30/30* (2006.01)
*G01N 30/88* (2006.01)

(52) U.S. Cl.
CPC ......... *B01D 15/161* (2013.01); *B01D 15/166* (2013.01); *B01D 15/1878* (2013.01); *B01J 20/24* (2013.01); *G01N 30/34* (2013.01); *B01J 2220/4825* (2013.01); *G01N 2030/3076* (2013.01); *G01N 2030/885* (2013.01)

(58) Field of Classification Search
USPC ............. 528/502, 480; 436/85; 73/61.55
See application file for complete search history.

(56) References Cited

U.S. PATENT DOCUMENTS

| | | | |
|---|---|---|---|
| 6,730,228 B2 | 5/2004 | Petro et al. | |
| 6,855,258 B2 | 2/2005 | Petro et al. | |
| 7,214,320 B1 | 5/2007 | Gregori et al. | |
| 8,076,147 B2 | 12/2011 | Damme et al. | |
| 8,318,896 B2 | 11/2012 | Winniford et al. | |
| 8,476,076 B2 | 7/2013 | Van Damme et al. | |
| 2010/0093964 A1 | 4/2010 | Van Damme et al. | |
| 2014/0090453 A1 | 4/2014 | Cong et al. | |

FOREIGN PATENT DOCUMENTS

| | | |
|---|---|---|
| WO | 2006081116 A1 | 8/2006 |
| WO | 2006127717 A1 | 11/2006 |

OTHER PUBLICATIONS

Albrecht et al., Macromol. Symp. 2007, pp. 46-55, vol. 257.
Albrecht et al., Macromolecules, 2007, pp. 5545-5551, vol. 40.
Chaimbault et al., Journal of Chromatography A, 1998, pp. 83-91, vol. 797.
Chitta et al., Journal of Chromatography A, 2010, pp. 7717-7722, vol. 1217, No. 49.
Edam et al., Branched-polymer separations using comprehensive two-dimensional molecular-topology fractionation x size-exclusion chromatography, Journal of Chromatography A, pp. 208-214, vol. 1201.
Findenegg et al., Adsorption from solution of large alkane and related molecules onto graphitized carbon, Carbon, 1987, pp. 119-128, vol. 25, No. 1.
Ginzburg et al., Journal of Chromatography A, 2010, pp. 6867-6874, vol. 1217, No. 44.
Hanai, Journal of Chromatography A, 2003, pp. 183-196, vol. 989.
Im, K et al., Journal of Chromatography A, 2009, pp. 4606-4610, vol. 1216.
Knox et al., Carbon-Based Packing Materials for Liquid Chromatography, pp. 73-119.
Lars-Christian Heinz et al., Polymer, 2005, pp. 12040-12045, vol. 46.
Leboda et al, Materials Chemistry and Physics, 1998, pp. 1-29, vol. 55.
Macko et al., Chromatographia, Aug. 2006, pp. 183-190, vol. 64, No. 3,4.
Macko et al., Journal of Chromatography A, 2003, pp. 55-62, vol. 1002.
Macko et al., Journal of Chromatography A, 2006, pp. 81-87, vol. 1115.
Macko et al., Journal Sep. Sci., 2003, pp. 1569-1574, vol. 26.

(Continued)

*Primary Examiner* — Terressa Boykin

(57) ABSTRACT

The invention provides methods for chromatography of a polyolefin polymer, comprising introducing a solution of the polyolefin polymer into a liquid flowing through a liquid chromatography stationary phase, the liquid chromatography stationary phase comprising graphitic carbon. The invention also provides an apparatus for polyolefin polymer chromatography, comprising a liquid chromatography stationary phase, the liquid chromatography stationary phase comprising graphitic carbon and at least one inert filler.

14 Claims, 9 Drawing Sheets

(56) References Cited

OTHER PUBLICATIONS

Boykin/ Macko et al., Macromolecular Symposia, 2010, pp. 182-190, vol. 298.

Macko et al., Macromolecules, 2009, pp. 6063-6067, vol. 42.

Macko et al., Sep. Sci., 2005, pp. 59-64, vol. 28.

Macko et al., Separation of porpene/1-alkene and ethylene/1-alkene copolymers by high-temperature adsorption liquid chromatography, Polymer, 2009, pp. 5443-5448, vol. 50, No. 23.

Marin et al., Journal of Chromatography A, 2004, pp. 255-262, vol. 1030.

Meunier et al., Characterization of long chain branched polymers by 2-D molecular topology fractionation X size-exclusion chromatography, Abstracts of Papers, Apr. 6-10, 235th, 2008ACD National Meeting, New Orleans, LA, United States.

Meunier et al., Molecular topology fractionation of polystyrene stars and long chain branched polyethylene fractions, Macromolecular Symposia, 2007, pp. 56-70, vol. 257.

Meunier et al., Two dimensional molecular topology fractionation X size-exclusion chromatography for characterization of long chain branched polymers, Polymer Preprints, 2008, pp. 131-132, vol. 49, No. 1, American Chemical Society, Division of Polymer Chemistry.

Mockel et al., Journal of Liquid Chromatography, 1991, pp. 2477-2498, vol. 14, No. 13.

Pasch et al., Pure and Applied Chem., 2008, pp. 1747-1762, vol. 80, No. 8.

Pereira et al., Journal of Separation Sci., 2007, pp. 1115-1124, vol. 30, No. 8.

Ross et al., Packing Materials for LC: Applications, Carbon-Based Packing Materials for Liquid Chromatography, pp. 121-161.

Roy et al., Macromolecules, 2010, pp. 3710-3720, vol. 43, No. 8.

Schoenmakers et al., A protocol for designing comprehensive two-dimensional liquid chromatography separation systems, Journal of Chromatography A, 2006, pp. 282-290, vol. 1120.

Stokich et al., 2-D molecular topology fractionation (MTF) X size-exclusion chromatography (SEC) system development and application to branched polyethylene polymers, Abstracts of Papers, Aug. 17-21, 2008, 236th, ACS National Meeting, Philadelphia, PA, United States.

PCT/US2010/061526, International Search Report.

PCT/US2010/061526, International Preliminary Report on Patentability.

PCT/US2010/061526, Written Opinion of the International Searching Authority.

Stoll et al., Fast, comprehensive two-dimensional liquid chromatography, Journal of Chromatography A, 2007, pp. 3-43, vol. 4468.

Technical Guide—HypercarbTM HPLC Columns, pp. 1-8, Thermo Electron Corporation.

Wang et al., Macromolecules, Dec. 2005, pp. 10341-10345, vol. 38, No. 25.

Wang et al., A graphical method for understanding the kinetics of peak capacity production in gradient elution liquid chromatography, Journal of Chromatography A, 2006, pp. 177-181, vol. 1125.

CHROMATOGRAPHY OF POLYOLEFIN POLYMERS

REFERENCE TO RELATED APPLICATIONS

This application is a 371 Application of International Application No. PCT/US2010/061526, filed on Dec. 21, 2010, which claims priority to U.S. application Ser. No. 12/643,111 filed on Dec. 21, 2009, pending, and fully incorporated herein by reference.

BACKGROUND OF THE INVENTION

The disclosed invention is in the field of liquid chromatography. Liquid chromatography is used by the art to analyze polymers, with regard to molecular size, by Size Exclusion Chromatography (SEC), and, with regard to chemical composition, by High Performance Liquid Chromatography (HPLC). This disclosure relates to HPLC analysis of polymers with regard to chemical composition.

Polyolefin polymers (such as polymers and copolymers comprising polymerized ethylene monomer and/or propylene monomer) have long been analyzed with regard to chemical composition distribution by temperature rising elution fractionation (TREF) and crystallization analysis fractionation (CRYSTAF). However, neither TREF nor CRYSTAF can be used to analyze amorphous polyolefin polymers. Furthermore, both TREF and CRYSTAF require a relatively long analysis time. Therefore, the art turned to HPLC in an attempt to reduce analysis time and to expand the scope of analysis to amorphous polymers. Macko et al. apparently were the first to do so in 2003 by studying the retention of polyethylene standards on silica and zeolite stationary phases (J. Chrom. A, 1002 (2003) 55). Wang, et al. studied the retention of polyethylene and polypropylene by zeolites in 2005 (Macromolecules, V. 38, No. 25 (2005) 10341). Heinz and Pasch used a silica stationary phase to analyze polyethylene-polypropylene blends by HPLC (Polymer 46 (2005) 12040). Albrecht, et al., used a silica stationary phase to analyze ethylene-vinyl acetate copolymers by HPLC (Macromolecules 2007, 40, 5545). Albrecht, et al., used a silica stationary phase to analyze ethylene-propylene copolymers by HPLC (Macromol. Symp. 2007, 257, 46).

Some chromatography separations using graphite are disclosed in the following references: Macko et al., *Separation of Propene/1-Alkene and Ethylene/1-Alkene Copolymers by High-Temperature Adsorption Liquid Chromatography*, Polymer 50 (2009), 5443-5448; Macko et al., *Separation of Linear Polyethylene from Isotactic, Atactic, and Syndiotactic Polypropylene by High-Temperature Adsorption Liquid Chromatography*, Macromolecules (2009), 42, 6063-6067; Chitta et al., *Elution Behavior of Polyethylene and Polypropylene Standards on Carbon Sorbents*, Journal of Chromatography A, 1217 (2010) 7717-7722; Findenegg et al., *Adsorption from Solution of Large Alkane and Related Molecules onto Graphitized Carbon*, Carbon, Vol 25, No. 1, (1987), 119-128; and Yin et al., *Theoretical Study of the Effects of Intermolecular Interactions in Self-Assembled Long-Chain Alkanes Adsorbed on Graphite Surfaces*, Surface and Interface Analysis (2001), 32, 248-252. See also U.S. Publication No. 2010/0093964. Other two dimensional chromatography with or without graphite are disclosed in the following: Roy et al., *Development of Comprehensive Two-Dimensional High Temperature Liquid Chromatography×Gel Permeation Chromatography for Characterization of Polyolefins*, Macromolecules (2010), 43, 3710-3720; and Ginzburg et al., *High-Temperature Two-dimensional Liquid Chromatography of Ethylene-Vinylacetate Copolymers*, Journal of Chromatography A, 1217 (2010), 6867-6874.

A remaining problem for the HPLC analysis of polyolefin polymers is the limited separation efficiency obtained by the prior art methods. There remains a need for new chromatographic methods for polyolefin polymers that provide improved separation efficiencies and reduced analysis times. These needs and others have been met by the following invention.

SUMMARY OF THE INVENTION

The invention provides a method for one-dimensional chromatography of a polyolefin polymer, comprising introducing a solution of the polyolefin polymer into a liquid flowing through a liquid chromatography stationary phase, the liquid chromatography stationary phase comprising graphitic carbon, and wherein the polyolefin polymer emerging from the liquid chromatography stationary phase has a retention factor greater than zero, and wherein the solution introduced into the liquid chromatography stationary phase is subjected to a temperature gradient, and/or the solution is subjected to a solvent gradient.

The invention also provides a method for multi-dimensional chromatography of a polyolefin polymer, comprising introducing a solution of the polyolefin polymer into a liquid flowing through a first liquid chromatography stationary phase or a field flow fractionation device, and subsequently flowing the solution through a second liquid chromatography stationary phase, the second liquid chromatography stationary phase comprising graphitic carbon, and wherein the polyolefin polymer emerging from the liquid chromatography stationary phase has a retention factor greater than zero.

The invention also provides an apparatus for polyolefin polymer chromatography, comprising a liquid chromatography stationary phase, the liquid chromatography stationary phase comprising graphitic carbon and at least one inert filler.

DETAILED DESCRIPTION

Figure 1A:
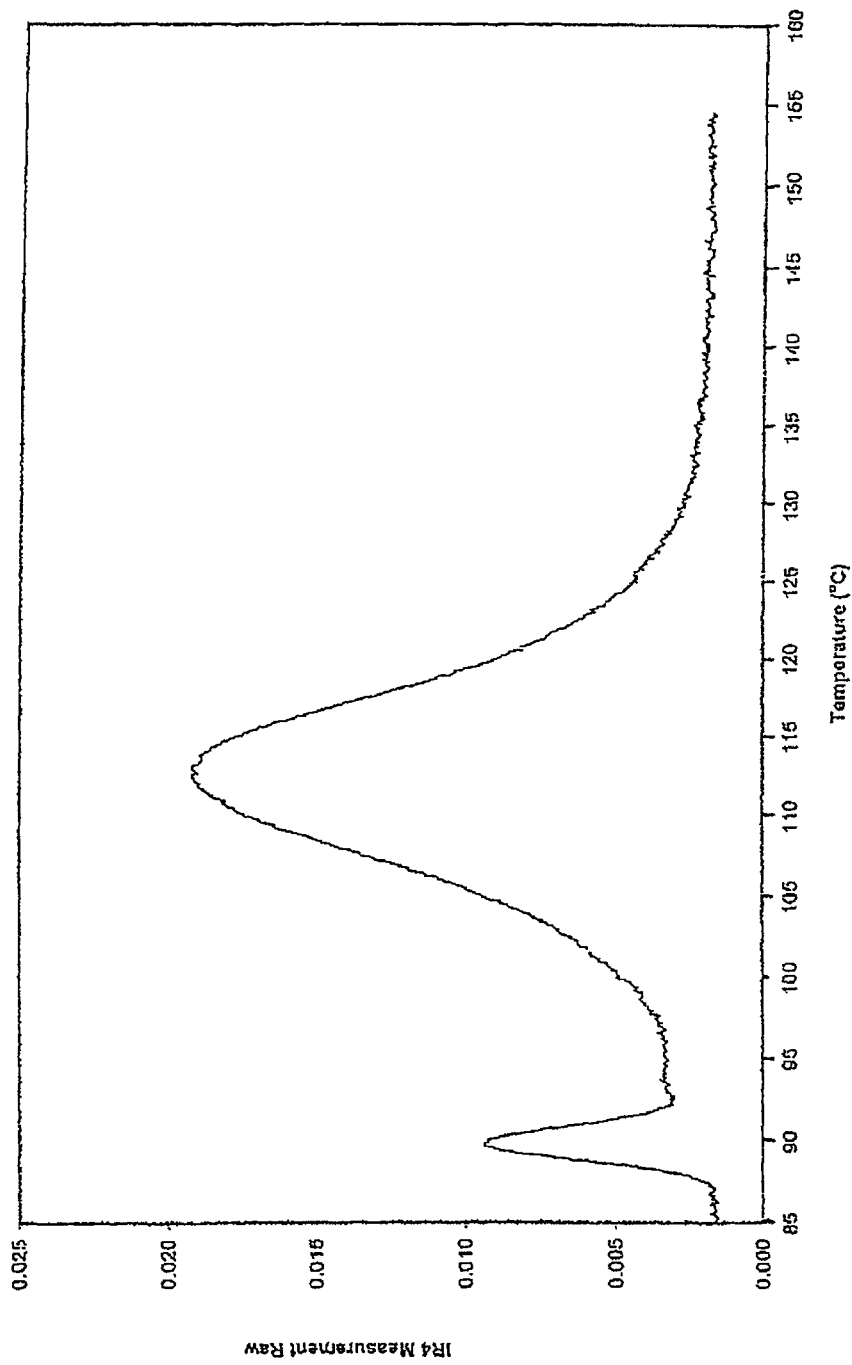
FIG. 1A is a TGIC (Thermal Gradient Interaction Chromatography) chromatogram of a metallocene polymerized ethylene-octene polymer.

As discussed above, the invention provides a method for one-dimensional chromatography of a polyolefin polymer, comprising introducing a solution of the polyolefin polymer into a liquid flowing through a liquid chromatography stationary phase, the liquid chromatography stationary phase comprising graphitic carbon, and wherein the polyolefin polymer emerging from the liquid chromatography stationary phase has a retention factor greater than zero, and wherein the solution introduced into the liquid chromatography stationary phase is subjected to a temperature gradient, and/or the solution is subjected to a solvent gradient.

In one embodiment, the solution introduced into the liquid chromatography stationary phase is subjected to a temperature gradient. In a further embodiment, the temperature gradient is greater than, or equal to 1° C. per minute, preferably greater than, or equal to 2° C. per minute, more preferably greater than, or equal to 3° C. per minute.

In one embodiment, the solution introduced into the liquid chromatography stationary phase is subjected to a solvent gradient.

In one embodiment, the solution introduced into the liquid chromatography stationary phase is subjected to both a temperature gradient and a solvent gradient. In a further embodiment, the temperature gradient is greater than, or equal to 1° C. per minute, preferably greater than, or equal to 2° C. per minute, more preferably greater than, or equal to 3° C. per minute.

In one embodiment, the liquid chromatographic stationary phase further comprises at least one inert filler. Inert fillers include, but are not limited to, inorganic materials, such as, but not limited to, glass, stainless steel, and copper. As used herein, the term "inert" refers to a material that does not chemically react with polymer solution or eluent, each used in the chromatographic process.

In one embodiment, the stationary phase comprises greater than, or equal to 50 weight percent of inert filler, preferably greater than, or equal to 60 weight percent of the inert filler, based on the sum weight of the inert filler and graphitic carbon.

In one embodiment, the inert filler is in the form of spheres. In a further embodiment, the spheres have a diameter from 10 to 150 microns, or from 15 to 100 microns, or from 20 to 50 microns.

In one embodiment, the at least one inert filler is glass.

In one embodiment, the stationary phase comprises greater than, or equal to 50 weight percent glass, preferably greater than, or equal to 60 weight percent glass, based on the sum weight of the glass and graphitic carbon.

In one embodiment, the glass is in the form of spheres. In a further embodiment, the spheres have a diameter from 10 to 150 microns, or from 15 to 100 microns, or from 20 to 50 microns.

In one embodiment, the stationary phase is contained in a column that has an L/D ratio greater than 8, preferably greater than 20, more preferably greater than 50, more preferably greater than 100, preferably greater than 200, and even more preferably greater than 400, where L=column length, and D=external diameter of the column.

The stationary phase may comprise a combination of two or more embodiments as described herein.

In one embodiment, the polyolefin polymer is an ethylene-based polymer.

In one embodiment, the polyolefin polymer is an ethylene/alpha-olefin interpolymer. In a further embodiment, the alpha-olefin is a C3-C10 alpha-olefin, and preferably selected from propylene, 1-butene, 1-hexene, and 1-octene.

In one embodiment, the polyolefin polymer is an ethylene/alpha-olefin copolymer. In a further embodiment, the alpha-olefin is a C3-C10 alpha-olefin, and preferably selected from propylene, 1-butene, 1-hexene, and 1-octene.

In one embodiment, the polyolefin polymer polymer is a copolymer of ethylene and an alpha-olefin. In a further embodiment, the alpha-olefin is 1-octene.

In one embodiment, the polyolefin polymer is a polyethylene homopolymer.

In one embodiment, the polyolefin polymer is an propylene-based polymer.

In one embodiment, the polyolefin polymer is an propylene/alpha-olefin interpolymer. In a further embodiment, the alpha-olefin is a C2, or C4-C10 alpha-olefin, and preferably selected from ethylene, 1-butene, 1-hexene, and 1-octene. As used herein, ethylene is referred to as an alpha-olefin.

In one embodiment, the polyolefin polymer is an propylene/alpha-olefin copolymer. In a further embodiment, the alpha-olefin is a C2, or C4-C10 alpha-olefin, and preferably selected from ethylene, 1-butene, 1-hexene, and 1-octene.

In one embodiment, the polyolefin polymer is a copolymer of propylene and an alpha-olefin. In a further embodiment, the alpha-olefin is ethylene.

In one embodiment, the polyolefin polymer is a polypropylene homopolymer.

In one embodiment, the polyolefin polymer has a concentration in the solution of polyolefin polymer of greater than 0.1 milligrams per milliliter of solution.

In one embodiment, the polyolefin polymer has a density less than, or equal to, 0.92 g/cc; or less than, or equal to, 0.90 g/cc; or less than, or equal to, 0.88 g/cc (1 cc=1 cm$^3$).

In one embodiment, the polyolefin polymer has a density less than, or equal to, 0.89 g/cc; or less than, or equal to, 0.88 g/cc; or less than, or equal to, 0.87 g/cc (1 cc=1 cm$^3$).

In one embodiment, the polyolefin polymer has a density from 0.83 g/cc to 0.97 g/cc, or from 0.84 g/cc to 0.95 g/cc, or from 0.85 g/cc to 0.93 g/cc (1 cc=1 cm$^3$).

In one embodiment, the polyolefin polymer comprises from 1 mole percent to 49 mole percent of an alpha-olefin, as determined by 13C NMR. Preferred alpha-olefins are discussed above.

In one embodiment, the polyolefin polymer comprises from 2 mole percent to 49 mole percent of an alpha-olefin, as determined by 13C NMR. Preferred alpha-olefins are discussed above.

In one embodiment, the polyolefin polymer comprises from 5 mole percent to 49 mole percent of an alpha-olefin, as determined by 13C NMR. Preferred alpha-olefins are discussed above.

The polyolefin polymer may comprise a combination of two or more embodiments as described herein.

In one embodiment, the chromatography stationary phase is contained within a GPC column.

The mobile phase (eluent) is any solvent or solvent mixture that will dissolve the polyolefin polymer at issue. In one embodiment, the mobile phase is one or more aromatic halohydrocarbons, for example, one or more aromatic chlorohydrocarbons. Examples include, but are not limited to, TCB (1,2,4-trichlorobenzene), ODCB (ortho-dichlorobenzene), and combinations thereof.

An inventive method may comprise a combination of two or more embodiments as described herein.

The invention also provides a method for multi-dimensional chromatography of a polyolefin polymer, comprising introducing a solution of the polyolefin polymer into a liquid flowing through a first liquid chromatography stationary phase or a field flow fractionation device, and subsequently flowing the solution through a second liquid chromatography stationary phase, the second liquid chromatography stationary phase comprising graphitic carbon, and wherein the polyolefin polymer emerging from the liquid chromatography stationary phase has a retention factor greater than zero.

In one embodiment, the solution of the polyolefin polymer solution is introduced into a liquid flowing through the first liquid chromatography stationary phase.

In one embodiment, the solution of the polyolefin polymer solution is introduced into a liquid flowing through the field flow fractionation device.

In one embodiment, the solution introduced into the first, or second, or both, liquid chromatography stationary phase(s), is/are subjected to a temperature gradient.

In a further embodiment, each temperature gradient is independently greater than, or equal to 1° C. per minute, preferably greater than, or equal to 2° C. per minute, more preferably greater than, or equal to 3° C. per minute.

In one embodiment, the solution introduced into the first, or second, or both, liquid chromatography stationary phase(s), is/are subjected to a solvent gradient.

In one embodiment, the solution introduced into the first, or second, or both, liquid chromatography stationary phase(s), is/are subjected to both a temperature gradient and a solvent gradient. In a further embodiment, each temperature gradient is independently greater than, or equal to 1° C. per minute, preferably greater than, or equal to 2° C. per minute, more preferably greater than, or equal to 3° C. per minute.

In one embodiment, the solution introduced into the first liquid chromatography stationary phase is subjected to a temperature gradient. In a further embodiment, the temperature gradient is greater than, or equal to 1° C. per minute, preferably greater than, or equal to 2° C. per minute, more preferably greater than, or equal to 3° C. per minute.

In one embodiment, the solution introduced into the second liquid chromatography stationary phase is subjected to a temperature gradient. In a further embodiment, the temperature gradient is greater than, or equal to 1° C. per minute, preferably greater than, or equal to 2° C. per minute, more preferably greater than, or equal to 3° C. per minute.

In one embodiment, the solution introduced into the first liquid chromatography stationary phase is subjected to a solvent gradient.

In one embodiment, the solution introduced into the second liquid chromatography stationary phase is subjected to a solvent gradient.

In one embodiment, the solution introduced into the first liquid chromatography stationary phase is subjected to a temperature gradient and a solvent gradient. In a further embodiment, the temperature gradient is greater than, or equal to 1° C. per minute, preferably greater than, or equal to 2° C. per minute, more preferably greater than, or equal to 3° C. per minute.

In one embodiment, the solution introduced into the second liquid chromatography stationary phase is subjected to a temperature gradient and a solvent gradient. In a further embodiment, the temperature gradient is greater than, or equal to 1° C. per minute, preferably greater than, or equal to 2° C. per minute, more preferably greater than, or equal to 3° C. per minute.

In one embodiment, the solution introduced into the first liquid chromatography stationary phase and the solution introduced into the second liquid chromatography stationary phase are both subjected to a temperature gradient. In a further embodiment, the temperature gradient is greater than, or equal to 1° C. per minute, preferably greater than, or equal to 2° C. per minute, more preferably greater than, or equal to 3° C. per minute.

In one embodiment, the solution introduced into the first liquid chromatography stationary phase and the solution introduced into the second liquid chromatography stationary phase are subjected to a solvent gradient.

In one embodiment, the solution introduced into the first liquid chromatography stationary phase and the solution introduced into the second liquid chromatography stationary phase are subjected to a temperature gradient and a solvent gradient. In a further embodiment, the temperature gradient is greater than, or equal to 1° C. per minute, preferably greater than, or equal to 2° C. per minute, more preferably greater than, or equal to 3° C. per minute.

In one embodiment, the polyolefin polymer has a concentration in the solution of polyolefin polymer of greater than 0.1 milligrams per milliliter of solution.

In one embodiment, the second liquid chromatography stationary phase consists essentially of graphitic carbon.

In one embodiment, the second liquid chromatography stationary phase is contained within a GPC column.

In one embodiment, the first liquid chromatography stationary phase comprises graphitic carbon.

In one embodiment, the first liquid chromatography stationary phase consists essentially of graphitic carbon.

In one embodiment, the first liquid chromatography stationary phase is contained within a GPC column.

In one embodiment, the first and/or the second liquid chromatographic stationary phase(s) further comprise(s) at least one inert filler. Inert fillers include, but are not limited to, inorganic materials, such as, but not limited to, glass, stainless steel, and copper. As used herein, the term "inert" refers to a material that does not chemically react with polymer solution or eluent, each used in the chromatographic process.

In one embodiment, the first liquid chromatographic stationary phase further comprises at least one inert filler. Inert fillers include, but are not limited to, inorganic materials, such as, but not limited to, glass, stainless steel, and copper.

In one embodiment, the second liquid chromatographic stationary phase further comprises at least one inert filler. Inert fillers include, but are not limited to, inorganic materials, such as, but not limited to, glass, stainless steel, and copper.

In one embodiment, the first and the second liquid chromatographic stationary phases, independently, further comprise at least one inert filler. Inert fillers include, but are not limited to, inorganic materials, such as, but not limited to glass, stainless steel, and copper beads.

In one embodiment, the first stationary phase comprises greater than, or equal to 50 weight percent inert filler, preferably greater than, or equal to 60 weight percent inert filler, based on the sum weight of the inert filler and graphitic carbon. In one embodiment, inert filler is in the form of spheres. In a further embodiment, the spheres have a diameter from 10 to 150 microns, or from 15 to 100 microns, or from 20 to 50 microns.

In one embodiment, the at least one inert filler is glass.

In one embodiment, the first stationary phase comprises greater than, or equal to 50 weight percent glass, preferably greater than, or equal to 60 weight percent glass, based on the sum weight of the glass and graphitic carbon. In one embodiment, the glass is in the form of spheres. In a further embodiment, the spheres have a diameter from 10 to 150 microns, or from 15 to 100 microns, or from 20 to 50 microns.

In one embodiment, the second stationary phase comprises greater than, or equal to 50 weight percent inert filler, preferably greater than, or equal to 60 weight percent inert filler, based on the sum weight of the inert filler and graphitic carbon. In one embodiment, the at least one filler is in the form of spheres. In a further embodiment, the spheres have a diameter from 10 to 150 microns, or from 15 to 100 microns, or from 20 to 50 microns.

In one embodiment, the at least one inert filler is glass.

In one embodiment, the second stationary phase comprises greater than, or equal to 50 weight percent glass, preferably greater than, or equal to 60 weight percent glass, based on the sum weight of the glass and graphitic carbon. In one embodiment, the glass is in the form of spheres. In a further embodiment, the spheres have a diameter from 10 to 150 microns, or from 15 to 100 microns, or from 20 to 50 microns.

In one embodiment, the first stationary phase and the second stationary phase, each, independently, comprises greater than, or equal to 50 weight percent inert filler, preferably greater than, or equal to 60 weight percent inert filler, based on the sum weight of the inert filler and graphitic carbon. In one embodiment, the inert filler is in the form of spheres. In a further embodiment, the spheres have a diameter from 10 to 150 microns, or from 15 to 100 microns, or from 20 to 50 microns.

In one embodiment, the at least one inert filler is glass.

In one embodiment, the first stationary phase and the second stationary phase each, independently, comprises greater than, or equal to 50 weight percent glass, preferably greater than, or equal to 60 weight percent glass, based on the sum weight of the glass and graphitic carbon. In one embodiment, the glass is in the form of spheres. In a further embodiment, the spheres have a diameter from 10 to 150 microns, or from 15 to 100 microns, or from 20 to 50 microns.

In one embodiment, the first stationary phase is contained in a column that has an L/D ratio greater than 8, preferably greater than 20, more preferably greater than 50, more preferably greater than 100, preferably greater than 200, and even preferably greater than 400, where L=column length, and D=external diameter of the column.

In one embodiment, the second stationary phase is contained in a column that has an L/D ratio greater than 8, preferably greater than 20, more preferably greater than 50, more preferably greater than 100, preferably greater than 200, and even more preferably greater than 400, where L=column length, and D=external diameter of the column.

In one embodiment, the first stationary phase and the second stationary phase are each, independently, contained in a column that has an L/D ratio greater than 8, preferably greater than 20, more preferably greater than 50, more preferably greater than 100, preferably greater than 200, and even more preferably greater than 400, where L=column length, and D=external diameter of the column.

The first stationary phase may comprise a combination of two or more embodiments as described herein.

The second stationary phase may comprise a combination of two or more embodiments as described herein.

In one embodiment, the polyolefin polymer is an ethylene-based polymer.

In one embodiment, the polyolefin polymer is an ethylene/alpha-olefin interpolymer. In a further embodiment, the alpha-olefin is a C3-C10 alpha-olefin, and preferably selected from propylene, 1-butene, 1-hexene, and 1-octene.

In one embodiment, the polyolefin polymer is an ethylene/alpha-olefin copolymer.

In a further embodiment, the alpha-olefin is a C3-C10 alpha-olefin, and preferably selected from propylene, 1-butene, 1-hexene, and 1-octene.

In one embodiment, the polyolefin polymer is a copolymer of ethylene and an alpha-olefin. In a further embodiment, the alpha-olefin is 1-octene.

In one embodiment, the polyolefin polymer is a polyethylene homopolymer.

In one embodiment, the polyolefin polymer is an propylene-based polymer.

In one embodiment, the polyolefin polymer is an propylene/alpha-olefin interpolymer. In a further embodiment, the alpha-olefin is a C2, or C4-C10 alpha-olefin, and preferably selected from ethylene, 1-butene, 1-hexene, and 1-octene. As used herein, ethylene is referred to as an alpha-olefin.

In one embodiment, the polyolefin polymer is an propylene/alpha-olefin copolymer. In a further embodiment, the alpha-olefin is a C2, or C4-C10 alpha-olefin, and preferably selected from ethylene, 1-butene, 1-hexene, and 1-octene.

In one embodiment, the polyolefin polymer is a copolymer of propylene and an alpha-olefin. In a further embodiment, the alpha-olefin is ethylene.

In one embodiment, the polyolefin polymer is a polypropylene homopolymer.

In one embodiment, the polyolefin polymer has a density less than, or equal to, 0.92 g/cc; or less than, or equal to, 0.90 g/cc; or less than, or equal to, 0.88 g/cc (1 cc=1 cm$^3$).

In one embodiment, the polyolefin polymer has a density less than, or equal to, 0.89 g/cc; or less than, or equal to, 0.88 g/cc; or less than, or equal to, 0.87 g/cc (1 cc=1 cm$^3$).

In one embodiment, the polyolefin polymer has a density from 0.83 g/cc to 0.97 g/cc, or from 0.84 g/cc to 0.95 g/cc, or from 0.85 g/cc to 0.93 g/cc (1 cc=1 cm$^3$).

In one embodiment, the polyolefin polymer comprises from 1 mole percent to 49 mole percent of an alpha-olefin, as determined by 13C NMR. Preferred alpha-olefins are discussed above.

In one embodiment, the polyolefin polymer comprises from 2 mole percent to 49 mole percent of an alpha-olefin, as determined by 13C NMR. Preferred alpha-olefins are discussed above.

In one embodiment, the polyolefin polymer comprises from 5 mole percent to 49 mole percent of an alpha-olefin, as determined by 13C NMR. Preferred alpha-olefins are discussed above.

The polyolefin polymer may comprise a combination of two or more embodiments as described herein.

In one embodiment, the first liquid chromatography stationary phase is contained within a GPC column.

In one embodiment, the second liquid chromatography stationary phase is contained within a GPC column.

In one embodiment, the first liquid chromatography stationary phase and the second liquid chromatography stationary phase are each, independently, contained within a GPC column.

The mobile phase (eluent) is any solvent or solvent mixture that will dissolve the polyolefin polymer at issue. In one embodiment, the mobile phase is one or more aromatic halohydrocarbons, for example, one or more aromatic chlorohydrocarbons. Examples include, but are not limited to, TCB (1,2,4-trichlorobenzene), ODCB (ortho-dichlorobenzene), and combinations thereof.

An inventive method may comprise a combination of two or more embodiments as described herein.

The invention also provides an apparatus for polyolefin polymer chromatography, comprising a liquid chromatography stationary phase, the liquid chromatography stationary phase comprising graphitic carbon and at least one inert filler.

In one embodiment, the apparatus further comprises a "temperature gradient device," and/or a "solvent gradient device." In a further embodiment, the temperature gradient is greater than, or equal to 1° C. per minute, preferably greater than, or equal to 2° C. per minute, more preferably greater than, or equal to 3° C. per minute.

In one embodiment, the apparatus further comprises a "temperature gradient device." In a further embodiment, the temperature gradient is greater than, or equal to 1° C. per minute, preferably greater than, or equal to 2° C. per minute, more preferably greater than, or equal to 3° C. per minute.

In one embodiment, the apparatus further comprises a "solvent gradient device."

In one embodiment, the apparatus further comprises a "temperature gradient device," and a "solvent gradient device." In a further embodiment, the temperature gradient is greater than, or equal to 1° C. per minute, preferably greater than, or equal to 2° C. per minute, more preferably greater than, or equal to 3° C. per minute.

A temperature gradient device (for example, a CEF from PolymerChar) is an instrument that is used to thermally treat, or cool, a column (for example, a chromatography column) in a controlled manner. A solvent gradient device (for example, as available from PolymerChar) is an instrument that is used to mix one or more solvents in a controlled manner, and wherein the solvent mixture is used as an eluent in a column (for example, a chromatography column).

Inert fillers include, but are not limited to, inorganic materials, such as, but not limited to, glass, stainless steel, and copper. As used herein, the term "inert" refers to a material that does not chemically react with polymer solution or eluent, each used in the chromatographic process.

In one embodiment, the stationary phase comprises greater than, or equal to 50 weight percent inert filler, preferably greater than, or equal to 60 weight percent inert filler, based on the sum weight of the inert filler and graphitic carbon.

In one embodiment, the inert filler is in the form of spheres. In a further embodiment, the spheres have a diameter from 10 to 150 microns, or from 15 to 100 microns, or from 20 to 50 microns.

In one embodiment, the at least one inert filler is glass.

In one embodiment, the stationary phase comprises greater than, or equal to 50 weight percent glass, preferably greater than, or equal to 60 weight percent glass, based on the sum weight of the glass and graphitic carbon.

In one embodiment, the glass is in the form of spheres. In a further embodiment, the spheres have a diameter from 10 to 150 microns, or from 15 to 100 microns, or from 20 to 50 microns.

In one embodiment, the stationary phase is contained in a column that has an L/D ratio greater than 8, preferably greater than 20, more preferably greater than 50, more preferably greater than 100, more preferably greater than 200, and even more preferably greater than 400, where L=column length, and D=external diameter of the column.

The stationary phase may comprise a combination of two or more embodiments as described herein.

In one embodiment, the polyolefin polymer is an ethylene-based polymer.

In one embodiment, the polyolefin polymer is an ethylene/alpha-olefin interpolymer. In a further embodiment, the alpha-olefin is a C3-C10 alpha-olefin, and preferably selected from propylene, 1-butene, 1-hexene, and 1-octene.

In one embodiment, the polyolefin polymer is an ethylene/alpha-olefin copolymer. In a further embodiment, the alpha-olefin is a C3-C10 alpha-olefin, and preferably selected from propylene, 1-butene, 1-hexene, and 1-octene.

In one embodiment, the polyolefin polymer is a copolymer of ethylene and an alpha-olefin. In a further embodiment, the alpha-olefin is 1-octene.

In one embodiment, the polyolefin polymer is a polyethylene homopolymer.

In one embodiment, the polyolefin polymer is an propylene-based polymer.

In one embodiment, the polyolefin polymer is an propylene/alpha-olefin interpolymer. In a further embodiment, the alpha-olefin is a C2, or C4-C10 alpha-olefin, and preferably selected from ethylene, 1-butene, 1-hexene, and 1-octene. As used herein, ethylene is referred to as an alpha-olefin.

In one embodiment, the polyolefin polymer is an propylene/alpha-olefin copolymer. In a further embodiment, the alpha-olefin is a C2, or C4-C10 alpha-olefin, and preferably selected from ethylene, 1-butene, 1-hexene, and 1-octene.

In one embodiment, the polyolefin polymer is a copolymer of propylene and an alpha-olefin. In a further embodiment, the alpha-olefin is ethylene.

In one embodiment, the polyolefin polymer is a polypropylene homopolymer.

In one embodiment, the polyolefin polymer has a density less than, or equal to, 0.92 g/cc; or less than, or equal to, 0.90 g/cc; or less than, or equal to, 0.88 g/cc (1 cc=1 $cm^3$).

In one embodiment, the polyolefin polymer has a density less than, or equal to, 0.89 g/cc; or less than, or equal to, 0.88 g/cc; or less than, or equal to, 0.87 g/cc (1 cc=1 $cm^3$).

In one embodiment, the polyolefin polymer has a density from 0.83 g/cc to 0.97 g/cc, or from 0.84 g/cc to 0.95 g/cc, or from 0.85 g/cc to 0.93 g/cc (1 cc=1 $cm^3$).

In one embodiment, the polyolefin polymer comprises from 1 mole percent to 49 mole percent of an alpha-olefin, as determined by 13C NMR. Preferred alpha-olefins are discussed above.

In one embodiment, the polyolefin polymer comprises from 2 mole percent to 49 mole percent of an alpha-olefin, as determined by 13C NMR. Preferred alpha-olefins are discussed above.

In one embodiment, the polyolefin polymer comprises from 5 mole percent to 49 mole percent of an alpha-olefin, as determined by 13C NMR. Preferred alpha-olefins are discussed above.

The polyolefin polymer may comprise a combination of two or more embodiments as described herein.

The mobile phase (eluent) is any solvent or solvent mixture that will dissolve the polyolefin at issue. In one embodiment, the mobile phase is one or more aromatic halo-hydrocarbons, for example, one or more aromatic chloro-hydrocarbons. Examples include, but are not limited to, TCB (1,2,4-trichlorobenzene), ODCB (ortho-dichlorobenzene), and combinations thereof.

In one embodiment, the chromatography stationary phase is contained within a GPC column.

An inventive apparatus may comprise a combination of two or more embodiments as described herein.

As discussed above, in one embodiment, the invention is a method for multi-dimensional chromatography of a polyolefin polymer, comprising introducing a solution of the polyolefin polymer into a liquid flowing through a first liquid chromatography stationary phase or a field flow fractionation device and subsequently flowing the solution through a second liquid chromatography stationary phase, the second liquid chromatography stationary phase comprising graphitic carbon, the polyolefin polymer emerging from the liquid chromatography stationary phase with a retention factor greater than zero, preferably wherein the solution introduced into the first or second, or both, liquid chromatography stationary phase(s) is subjected to a temperature gradient.

Also preferably, the solution introduced into the first, or second, or both, liquid chromatography stationary phase(s) can be subjected to a solvent gradient.

The solution introduced into the first, or second, or both, liquid chromatography stationary phase(s) can also be subjected to both a temperature and a solvent gradient. Preferably the polyolefin polymer is a copolymer consisting essentially of ethylene and an alpha-olefin, especially where the alpha-olefin consists essentially of 1-octene, or where the polyolefin polymer is a copolymer consisting essentially of propylene and an alpha-olefin. Also preferred is where the alpha-olefin consists essentially of ethylene. Desirably, the polyolefin polymer has a concentration in the solution of polyolefin polymer of greater than 0.1 milligrams per milliliter of solution.

The second liquid chromatography stationary phase preferably consists essentially of graphitic carbon. The first liquid chromatography stationary phase can also consist essentially of a GPC column or the second liquid chromatography stationary phase consists essentially of a GPC column.

Alternatively, the first liquid chromatography stationary phase can consist essentially of graphitic carbon.

In another embodiment, the invention is a method for one-dimensional chromatography of a polyolefin polymer, comprising introducing a solution of the polyolefin polymer into a liquid flowing through a liquid chromatography stationary phase, the liquid chromatography stationary phase comprising graphitic carbon, the polyolefin polymer emerging from the liquid chromatography stationary phase with a retention factor greater than zero, preferably, wherein the solution introduced into the liquid chromatography stationary phase is subjected to a temperature gradient, also preferably, wherein the solution introduced into the liquid chromatography stationary phase is subjected to a solvent gradient, or, wherein the solution introduced into the liquid chromatography stationary phase is subjected to both a temperature and a solvent gradient.

As discussed above, this disclosure provides a method for chromatography of a polyolefin polymer, comprising the step of: introducing a solution of the polyolefin polymer into a liquid flowing through a liquid chromatography stationary phase, the liquid chromatography stationary phase comprising graphitic carbon, the polyolefin polymer emerging from the liquid chromatography stationary phase with a retention factor greater than zero. The improvement of this disclosure centers on the use of a liquid chromatography stationary phase comprising graphitic carbon, in combination with the additional features described herein.

This disclosure also provides a method for determining the monomer to co monomer ratio of a copolymer consisting essentially of ethylene or propylene and an alpha olefin co monomer, comprising the steps of: (a) flowing a liquid mobile phase into contact with a liquid chromatography stationary phase comprising graphitic carbon to produce an effluent stream of liquid mobile phase from the stationary phase; (b) introducing a solution of the copolymer into the liquid mobile phase, so that the copolymer emerges in the effluent stream with a retention factor that varies as a mathematical function of the monomer to comonomer ratio of the copolymer.

The term "polyolefin polymer," in this disclosure is defined as all polymers and copolymers (including high pressure low density polyethylene (LDPE), heterogeneous polymers, random, block, and graft polymers, interpolymers and copolymers), comprising one or more polymerized monomers, selected from the group consisting of ethylene, an alpha olefin having from 3-20 carbon atoms (such as 1-propylene, 1-butene, 1-hexene, 1-heptene and 1-octene), 4-methyl-1-pentene, and/or acetylenically unsaturated monomers having from 2-20 carbons, and/or diolefins having from 4-18 carbons and any other monomer used in the art to modify the density of a polymer. Heterogeneous polymers include Ziegler-Natta polymerized polymers, such as LLDPE and HDPE, and include products such as DOWLEX™ Linear Low Density Polyethylene (LLDPE) made by The Dow Chemical Company. The random copolymers include those polymerized using metallocene or constrained geometry catalyst technology, and include polymers such as AFFINITY™ Polyolefin Plastomer and ENGAGE™ Polyolefin Elastomer, both available from The Dow Chemical Company, and EXACT™ Polyolefin available from Exxon-Mobil. Methods for polymerizing these random copolymers are well known in the art, and include those described in U.S. Pat. No. 5,272,236 and U.S. Pat. No. 5,278,272. The block copolymers include those polymerized using chain shuttling technology and two catalyst species, such as is disclosed in U.S. Pat. No. 7,355,089, and include polymers such as INFUSE™ Olefin Block Copolymers made by The Dow Chemical Company.

In addition, the term "polyolefin polymer" in this disclosure is defined as a polymer having an average molecular weight, as determined by light scattering, greater than 1,000 grams per mole (preferably greater than 2,000 grams per mole and more preferably greater than 4,000 grams per mole, and can be as high as 10 million grams per mole). The polyolefin polymer can be a copolymer consisting essentially of polymerized ethylene monomer and a polymerized alpha olefin monomer such as 1-octene. The polyolefin polymer can be a copolymer consisting essentially of polymerized propylene monomer and a polymerized alpha olefin monomer such as ethylene. Such propylene based polymers include homopolymer polypropylene, impact propylene based copolymers, and random propylene based copolymers. Other more specialized polymers also benefit from the method and apparatus disclosed herein and include ethylene/acrylic acid copolymers, ethylene/vinyl acetate copolymers and ethylene/styrene interpolymers, halogenated polymers, and polymers containing maleic anhydride moieties.

In most applications, the temperature of the solution of the polyolefin polymer, the temperature of the liquid chromatography stationary phase, and the temperature of the detector, will be controlled at an elevated temperature to increase the solubility of the polyolefin polymer; that is to render the polyolefin polymer soluble. The concentration of the polyolefin polymer in the solution of polyolefin polymer is preferably greater than 0.1 milligrams per milliliter of solution (mg/mL), especially greater than 2 mg/mL. The solvent used for the solution of the polyolefin polymer is preferably decanol when the polyolefin polymer is polyethylene or polypropylene. Any suitable liquid mobile phase can be used in the method of this disclosure. A temperature gradient mobile phase is preferred in the method of this disclosure. The temperature of the liquid chromatography stationary phase can be increased during the method of this disclosure and/or the solvent composition can be a gradient during this method. A mobile phase having no aliphatic hydrogen content (such as 1,2,4-trichlorobenzene) facilitates the use of an infrared detector for the method of this disclosure.

Any liquid chromatography stationary phase that comprises graphitic carbon can be used in the method of this disclosure. The term "graphitic carbon" in this disclosure is defined as all varieties of materials comprising the element carbon in the allotropic form of graphite, irrespective of the presence of structural defects, if the three-dimensional hexagonal crystalline long-range order of graphite can be detected in the material by diffraction methods (such as X-ray diffraction spectroscopy), independent of the volume fraction and the homogeneity of distribution of such crystalline domains. Carbon nanotubes and carbon "buckeyballs" are examples of forms of graphitic carbon that are useful in the method of this disclosure. Preferably, the liquid chromatography stationary phase consists essentially of graphitic carbon, especially porous graphitic carbon. The graphitic carbon is usually packed into columns and comprises flat sheets of hexagonally arranged carbon atoms at the molecular level. In one embodiment, the graphitic carbon has a particle size of from about 1 to about 10 microns, preferably an average particle size of about 3 microns, or 5 microns or 7 microns, and preferably has an average pore size of about 200 to about 300 Angstroms, more preferably an average pore size of about 250 Angstroms. In one embodiment, the internal surface of the graphitic carbon has an area from about 10 to about 140 square meters/gram, or from about 50 to about 140 square meters/gram, or from about 100 to about 140 square meters/gram, and preferably about 120 square meters/gram. In one embodiment, the length of the columns is typically from about 30 mm to about 100 mm, and diameter of the column is from about 2 mm to about 5 mm.

An example of a commercially available liquid chromatography stationary phase that consists essentially of graphitic carbon includes the HYPERCARB brand HPLC column from Thermo Scientific, Waltham Mass. An example of a commercially available liquid chromatography stationary phase that comprises graphitic carbon includes the DISCOVERY ZR-CARBON brand HPLC column from Sigma Aldrich, St. Louis, Mo. Leboda, et al, Materials Chemistry and Physics 55 (1998) pages 1-29, provides a literature review of HPLC carbon adsorbents.

The method of this disclosure can be coupled, on or off line, with other analytical methods. For example, the effluent from an SEC column containing an ethylene 1-octene polyolefin copolymer of a selected molecular size can be analyzed by the method of this disclosure to determine the ratio of ethylene to 1-octene of the copolymer of the selected molecular size. See also Roy et al., *Development of Comprehensive Two-Dimensional High Temperature Liquid Chromatography×Gel Permeation Chromatography for Characterization of Polyolefins*, Macromolecules (2010), 43, 3710-3720; incorporated herein by reference.

The method of this disclosure could be scaled up to include large scale fractionations of many grams or many pounds of polymer by scaling up the size of the apparatus and the graphitic column.

This disclosure could include a temperature gradient, in addition to, and/or, a solvent gradient, as a way to perform the fractionation.

In addition this disclosure could include a fractionation in a commercial process to refine the purity of the comonomer distribution of the commercial product.

The crystallization elution fractionation (CEF) technique relies upon dynamic crystallization of polymer from a moving carrier. The crystallization substrate is normally spherical glass beads or perhaps stainless steel shot, and is more or less inert with respect to physical interaction with the polymer. A modification of the technique substitutes a more interactive substrate, in this case a carbon surface in a commercial column known as "Hypercarb," potentially possible packing materials of carbon nanotubes or silicon nanotubes for surface area and surface property, and does not rely upon dynamic crystallization of the polymer. In other words, adsorption to the carbon surface at a fixed temperature has replaced dynamic crystallization. The new technique is known as thermal gradient interaction chromatography (TGIC). Both CEF and TGIC rely upon a thermal gradient to elute polymer.

In order to investigate the mechanism of separation more fully, material is collected from the TGIC column for the purpose of further analysis and identification. Because the column eluent is relatively dilute with respect to the concentrations needed by instrumental techniques used for identification, such as NMR, it is necessary to make multiple injections, and collect and combine respective fractions.

DEFINITIONS

The term "polymer," as used herein, refers to a polymeric compound prepared by polymerizing monomers, whether of the same or a different type. The generic term polymer thus embraces the term homopolymer (employed to refer to polymers prepared from only one type of monomer, with the understanding that trace amounts of impurities can be incorporated into the polymer structure), and the term interpolymer as defined hereinafter.

The term "interpolymer," as used herein, refers to polymers prepared by the polymerization of at least two different types of monomers. The generic term interpolymer includes copolymers (employed to refer to polymers prepared from two different monomers), and polymers prepared from more than two different types of monomers.

The term "olefin-based polymer," as used herein, refers to a polymer that comprises a majority amount of polymerized olefin monomer, for example ethylene or propylene, (based on weight of the polymer) and, optionally, at least one comonomer.

The term "ethylene-based polymer," as used herein, refers to a polymer that comprises a majority amount of polymerized ethylene monomer (based on weight of the polymer) and, optionally, at least one comonomer.

The term "ethylene/α-olefin interpolymer," as used herein, refers to an interpolymer that comprises a majority amount of polymerized ethylene monomer (based on the weight of the interpolymer) and at least one α-olefin.

The term, "ethylene/α-olefin copolymer," as used herein, refers to a copolymer that comprises a majority amount of polymerized ethylene monomer (based on the weight of the copolymer), and an α-olefin, as the only two monomer types.

The term "propylene-based polymer," as used herein, refers to a polymer that comprises a majority amount of polymerized propylene monomer (based on weight of the polymer) and, optionally, at least one comonomer.

The term "propylene/α-olefin interpolymer," as used herein, refers to an interpolymer that comprises a majority amount of polymerized propylene monomer (based on the weight of the interpolymer) and at least one α-olefin.

The term, "propylene/α-olefin copolymer," as used herein, refers to a copolymer that comprises a majority amount of polymerized propylene monomer (based on the weight of the copolymer), and an α-olefin, as the only two monomer types.

The term "composition," as used herein, includes a mixture of materials which comprise the composition, as well as reaction products and decomposition products formed from the materials of the composition.

The term "multidimensional chromatography," as used herein, refers to the coupling together of multiple separation mechanisms (for example, see "J. C. Giddings (1990), Use of Multiple Dimensions in Analytical Separations, in Hernan Cortes Editor, *Multidimensional Chromatography: Techniques and Applications* (1st ed. pp. 1), New York, N.Y.: Marcel Dekker, Inc.)".

Figure 8:
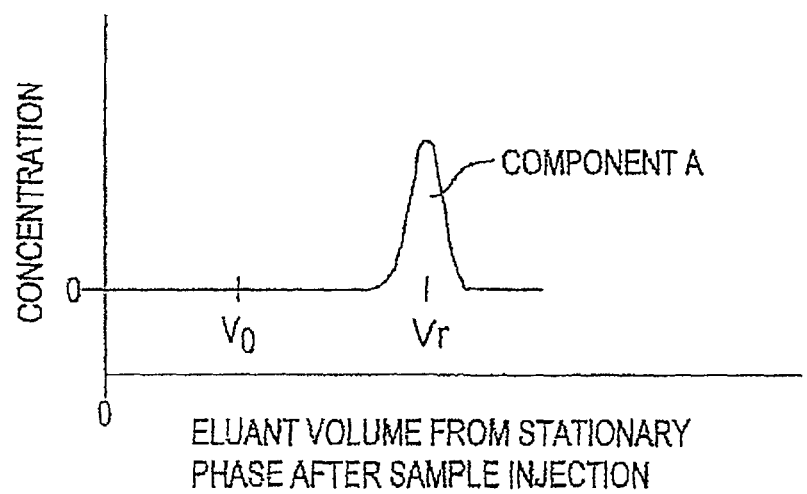
FIG. 8 depicts a theorized HPLC chromatogram of the elution of Component A at an elution volume peaking at Vr.

The term "retention factor" is defined as shown in FIG. 8. This figure represents a theorized HPLC chromatogram, and depicts the elution of Component A at an elution volume peaking at Vr. A low molecular weight unretained component eluting from the stationary phase would elute at $V_0$. The retention factor (k) for Component A is $(Vr-V_0) \div V_0$.

The term "chromatography stationary phase," as used herein, refers to a material which exists in the fluid stream (liquid or gas) of a chromatographic process, and which interacts with the analyte(s) and/or fluid stream of interest. As known in the art, the term "liquid" in the phrase "liquid chromatography stationary phase" refers to the type of chromatography method, for example a liquid chromatography method, such as HPLC or GPC.

The term "field-flow fractionation (FFF) device," as used herein, refers to a separation technique, where a field is applied to a mixture (for example, a polymer solution), perpendicular to the mixture's flow, in order to cause separation due to differing mobilities of the various components (for example, polymer components) in the field. See also "Giddings, Yang, and Myers, Flow-field-flow Fractionation: A Versatile New Separation Method." Science 193.4259 (1976): 1244-1245."

The terms "comprising," "including," "having," and their derivatives, are not intended to exclude the presence of any additional component, step or procedure, whether or not the same is specifically disclosed. In order to avoid any doubt, all compositions claimed through use of the term "comprising" may include any additional additive, adjuvant, or compound, whether polymeric or otherwise, unless stated to the contrary. In contrast, the term, "consisting essentially of" excludes from the scope of any succeeding recitation any other component, step or procedure, excepting those that are not essential to operability. The term "consisting of" excludes any component, step or procedure not specifically delineated or listed.

Test Methods

Polymer density was measured in accordance with ASTM D-792-08.

Melt index (I2) of an ethylene-based polymer is measured in accordance with ASTM D-1238-04, condition 190° C./2.16 kg. For propylene-based polymers, the melt flow rate (MFR) is measured in accordance with ASTM D-1238-04, condition 230° C./2.16 kg.

EXPERIMENTAL

Example 1

A metallocene polymerized ethylene-octene copolymer product (EO-1) is chosen for fractionation. EO-1 has a melt index of 0.82 g/10 minutes and a density of 0.885 g/cm³. The sample for use in TGIC (Thermal Gradient Interactive Chromatography) is prepared by weighing approximately 32 mg of polymer into a "10 ml" GC glass vial, which is capped, and placed in a Crystallization Elution Fractionation (CEF) (PolymerChar, Spain) auto sampler. The instrument adds o-dichlorobenzene (ODCB), containing 300 ppm butylated hydroxytoluene (BHT) as an oxidation inhibitor, to the vial, producing a solution that is approximately "4 mg/mL" in polymer. The dissolution is done by the autosampler at 160° C. for 90 minutes. The CEF is equipped with an IR-4 detector operating at 150° C. The delay volume (the volume that the first polymer fraction has to travel before reaching the detector) is 1.5 ml.

The column is a "10 cm long" HYPERCARB column, part number 35005-104646, and the mobile phase is ODCB. The injection volume is 300 μL, and the injection temperature is 150° C. The polymer solution is loaded onto the column at 110° C. The polymer solution is kept at 110° C. for two minutes, and then cooled down to 90° C., at 10° C./min, and kept at 90° C. for two minutes for thermal equilibrium. No solvent flow is used during the cooling and thermal equilibrium steps. Polymer solution is eluted from 90° C. to 165° C. at 3° C./min, at a flow rate of 0.7 ml/min. The chromatogram is shown in FIG. 1a.

Fraction collection is performed using a Spectra Chrom CF-1 fraction collector. The collector is operated in timed mode, changing collection vials every two minutes (every 6° C.). The vials are glass. A separate solvent line is used to connect the column directly to the fraction collector diverter valve. The CEF detector is bypassed. The collection is started manually, each time, at the moment when the temperature program and pump flow of the elution process are initiated. The same vials are used for each injection, so that the timed fractions are accumulated. A total of 12 fractions are collected from 90 to 165° C.

After 11 injections are completed, the twelve vials are capped with aluminum foil and placed in a vacuum oven at 140° C. to remove the ODCB. The evaporation of the solvent left a thin layer of polymer on the sides and bottom of the vials. The vials of fraction #1, 2, 3, 4, 5, 6, 7, 8 and 12 are submitted for ¹H NMR analysis.

The experimental conditions for ¹H NMR analysis are as follows: "1.4 g of tetrachloroethane-$d_2$ containing 0.001 M Cr(AcAc)$_3$" is added to the vial which contains the polymer. The solution is heated to 120° C. to wash off the polymer. The solution is transferred to a 10 mm NMR tube. The procedure is repeated twice. ¹H NMR is acquired with a 10 mm cryoprobe on a Bruker AV400 at 120° C. The residual water signal is very close to the signals from methine and methylene. In order to measure the octene content accurately, a new method, which reduces the effect of residual water, is developed. The method uses three drops of DMSO-$d_6$ to move the water signal down field to get relatively accurate signal integrals of methine and methylene. Two proton NMR spectra were acquired to get the octene content. The first is a regular ¹H NMR, the signal integral from methine and methylene is obtained after setting the integral of residual signal from TCE-$d_2$ to 100. The second is a ¹H NMR, with slight presaturation of the signal of methine and methylene to get more accurate integral of methyl relative to residual signal from TCE-$d_2$, which is set to 100 again. Octene content is calculated according to FIG. 2. The plot of the comonomer mol % of each fraction is plotted against the starting temperature of each fraction (see FIG. 1b).

Example 2

The thermal gradient interaction chromatography (TGIC) on polymerized ethylene-octene (EO) polymers and blends. EO-2 has a melt index of 1 g/10 minutes and a density of 0.865 g/cm³. EO-3 has a melt index of 66 g/10 minutes and a density of 0.882 g/cm³. Blend #1 is "50:50 (wt/wt) solution blend" of EO3 and a high density homopolymer polyethylene at a melt index of 1 g/10 min and a density of 0.953 g/cm³. Blend #2 is a "50:50 (wt/wt) solution blend" of isotactic polypropylene at MFR (ASTM D 1238 condition 2.16 kg/230° C.) of 13 g/10 minutes, and NIST SRM linear polyethylene 1484a.

The dissolution time is 120 minutes at 160° C. The polymer solutions are loaded onto the column at 100° C. The polymer solution is kept at 100° C., for two minutes, and then cooled down to 80° C., at 20° C./min, and kept at 80° C. for five minutes for thermal equilibrium. Polymer solution is eluted from 80° C. to 165° C., at 4° C./min, at a flow rate of 0.5 ml/min. Other experimental conditions are the same as Example 1. The chromatogram for EO-2, Blend #1 and #2 are shown in FIG. 3.

Figure 1B:
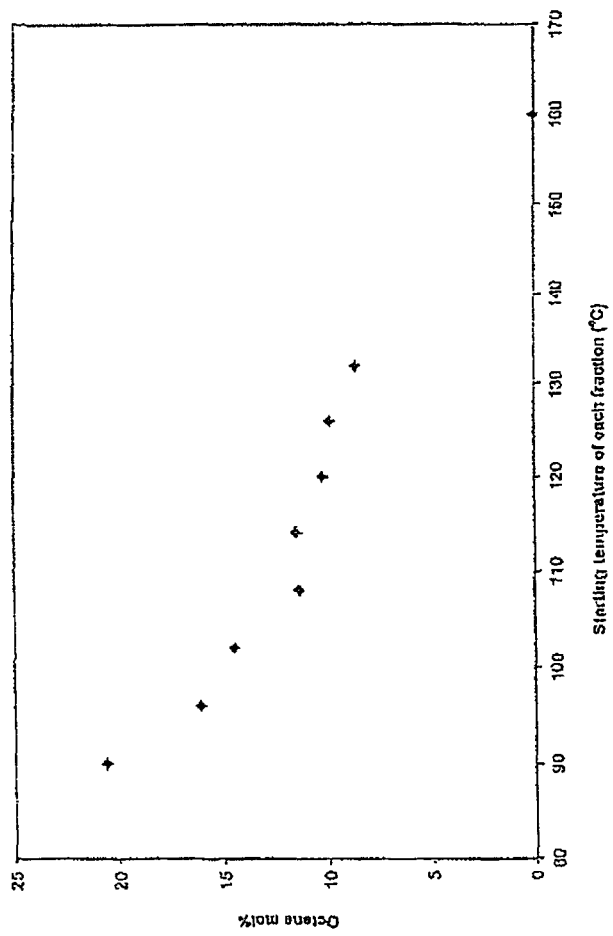
FIG. 1B is a plot of octene mol % in the fraction collected from TGIC of a metallocene polymerized ethylene-octene polymer.
Figure 2:
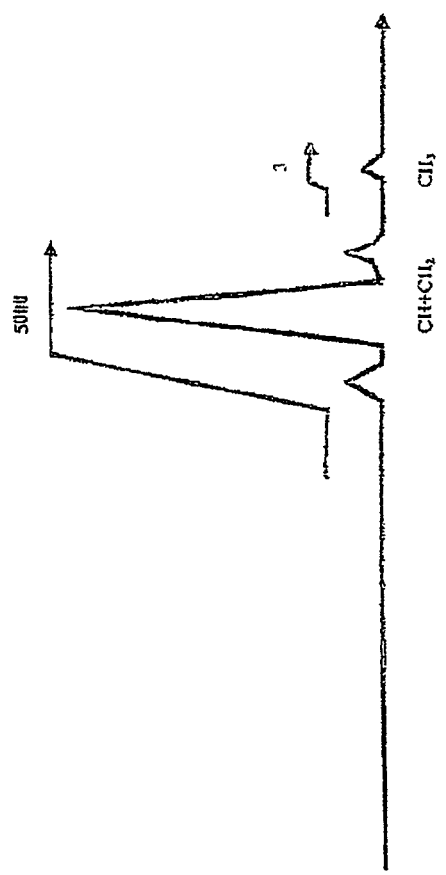
FIG. 2 shows a calculation of octene mol % from 1H NMR determined by assuming the end group effect is negligible.

To summarize, FIG. 1b shows the composition based separation of EO-1, which shows the comonomer content from 0 to at least 20 mole percent using the invention, whereas using prior art techniques, such as temperature rising elution fractionation (TREF) and crystallization fractionation (CRYSTAF), such separation on a wide range of comonomer content is not possible. Further, use of TGIC offers a fraction of the otherwise required analysis time for TREF or CRYSTAF. For example, about 30 minutes for a TGIC analysis, as compared to about 480 minutes for a TREF and about 300 minutes for CRYSTAF analysis.

Also since the fractionation mechanism is different from TREF and CRYSTAF (both based on crystallization ability), use of TGIC allows separation based on comonomer only, not cocrystallization effects. Since there is no solvent gradient, this opens a wide window of detectors for TGIC, such as commercially available light scattering detectors, viscometers and the IR-5 detector (PolymerChar). The other benefits of using TGIC is the freedom of using multiple detectors, light scattering detector (examples are multiple angle light scattering detectors, two-angle light scattering) IR-4 detectors with different wavelength filters, online viscometers (examples are two capillary viscometers, three viscometers), and online FT-IR detectors.

Figure 3:
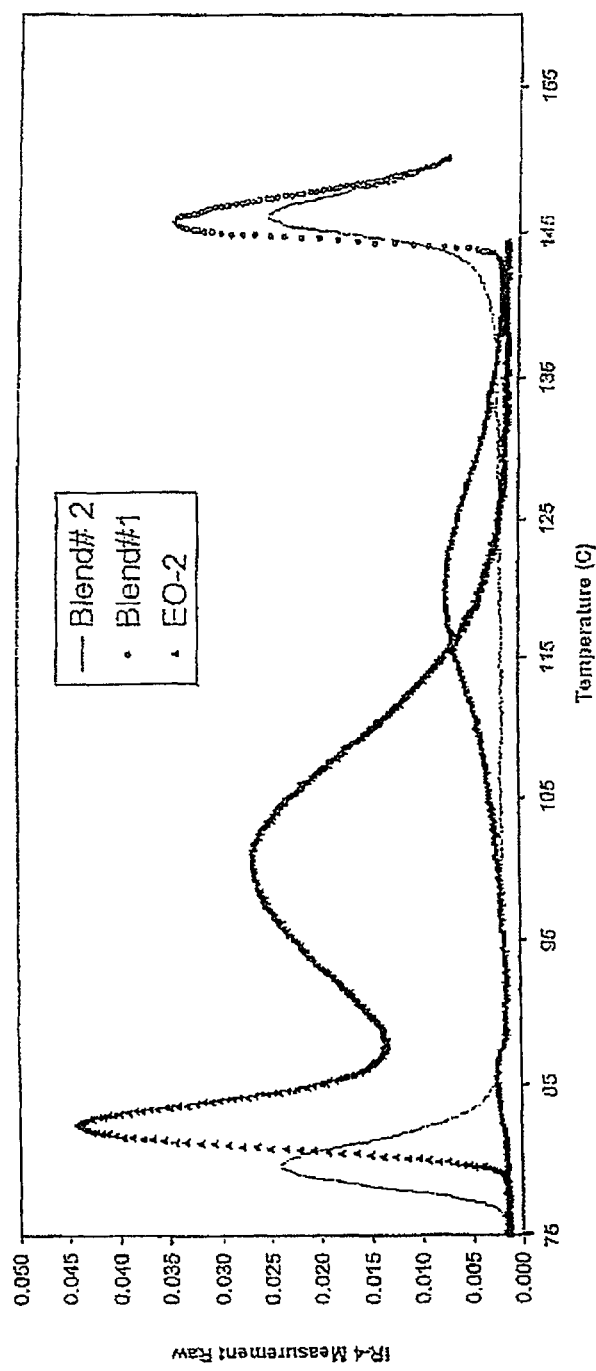
FIG. 3 is an overlay of TGIC chromatograms of polymers of EO-2, Blend #1, and Blend #2 using a graphitic carbon stationary phase.

FIG. 3 shows an improved resolution for polyolefin polymers with different composition. For example, for Blend #2, the separation between isotactic polypropylene and HDPE is at least 60° C., while ATREF would provide about a 20° C. separation, and CRYSTAF would have less than a 10° C. separation.

Example 3

Figure 4:
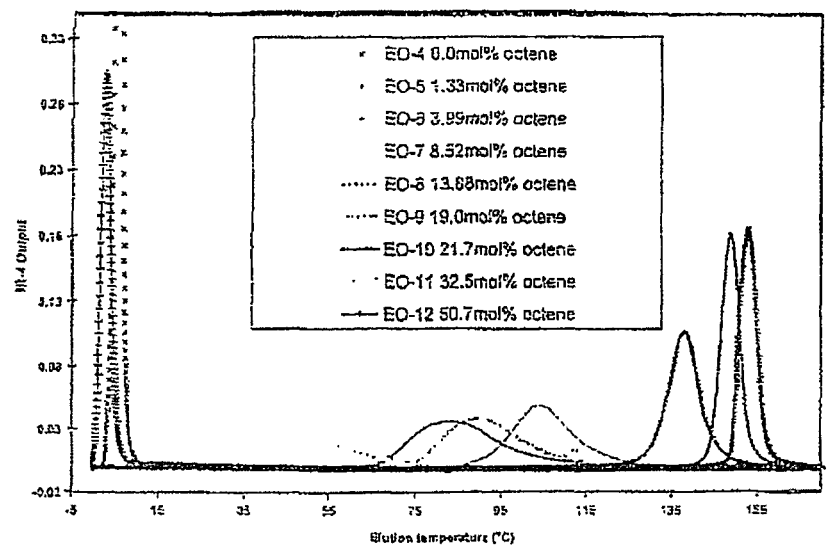
FIG. 4 is TGIC chromatograms of EO-4 to EO-12 polymers with HYPERCARB column.
Figure 5:
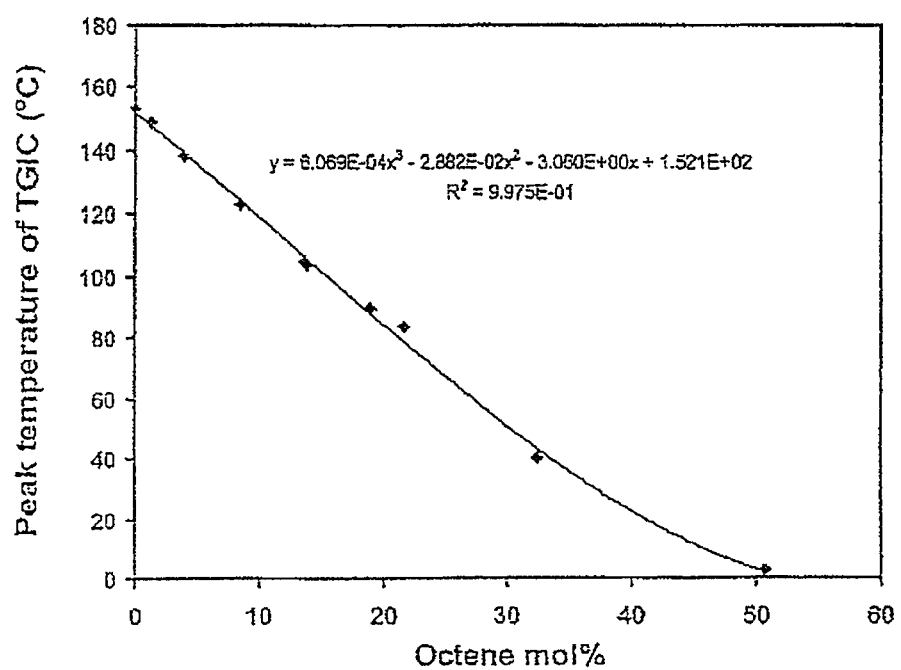
FIG. 5 is a plot of the peak temperature of TGIC chromatograms of EO-4 to EO-12 polymers versus octene mol %, by using HYPERCARB column.

Eight ethylene-octene (EO) copolymers (EO-4 to EO-11) and one octene-ethylene copolymer (EO-12) were polymerized by using CGC catalysts. The octene mole percent of each of the EO polymers (Table 1) were measured by $^{13}$C NMR. EO-4 to EO-12 are analyzed by TGIC with a HYPERCARB column (column dimension: 100 mm×4.6 mm, the particle size of 7 µm, and S/N:0501919K4), and a commercially available Crystallization Elution Fractionation (CEF) instrument (PolymerChar, Spain). The CEF is equipped with IR-4 detector. ODCB is used as solvent. The samples are prepared by the autosampler of CEF. The detailed experimental parameters, exported with the CEF instrument tool as an excel sheet, are listed in Table 2. The chromatograms of EO-4 to EO-12 are shown in FIG. 4. The peak temperature of chromatogram decreases with octene mol %. The peak temperature of elution is in an order of EO-12<EO-11<EO-10<EO-9<EO-8<EO-7<EO-6<EO-5<EO-4 (only the polymer fraction of EO-4 is accounted). Eicosane is soluble in ODCB at zero degree, thus showing as a soluble fraction for EO-4 blend). EO-12 with the highest octene mol % elutes at the lowest temperature, while EO-4 polymer fraction with zero octene mol % elutes at the highest temperature. The peak temperature of each chromatogram is plotted against octene mol % in FIG. 5. A correlation of the "peak temperature of TGIC chromatogram" versus the "octene mole percent" is obtained. This correlation covers a much higher octene range than other crystallization based techniques such as CEF, ATREF and CRYSTAF, which is usually less than 12 mole percent octene, based on the 13C NMR (see Randall, James C., JMS-Rev. Macromol. Chem. Phys., C29 (2&3), 201-317 (1989)).

TABLE 1

Octene mol % of EO-4 to EO-12

| Sample description | Octene mol % | Peak temperature of chromatogram (° C.) |
|---|---|---|
| EO-4 blended with Eicosane | 0.00 (Octene mol % is measured only for polymer portion, not Eicosane) | 153.11 |
| EO-5 | 1.33 | 148.93 |
| EO-6 | 3.99 | 138.21 |
| EO-7 | 8.52 | 123.22 |
| EO-8 | 13.88 | 103.76 |
| EO-9 | 19.00 | 89.75 |
| EO-10 | 21.70 | 83.47 |
| EO-11 | 32.50 | 39.89 |
| EO-12 | 50.70 | 2.44 |

TABLE 2

TGIC experimental conditions for EO-4 to EO-12 with HYPERCARB column

| Dissolution Time at 160° C. | min | 120 |
|---|---|---|
| Concentration | mg/ml | 2 |
| Loading loop volume | mL | 0.2 |
| Stabilization Temperature | ° C. | 140 |
| Stabilization Rate | ° C./min | 40 |
| Stabilization Time (Pre) | min | 2 |
| Stabilization Time (Post) | min | 2 |
| Crystallization Temperature | ° C. | 0 |
| Crystallization Rate | ° C./min | 6 |
| Crystallization Time | min | 2 |
| Soluble Fraction (SF) Time | min | 2 |
| Elution Temperature | ° C. | 175 |
| Elution Rate | ° C./min | 3 |
| Crystallization Pump Flow | mL/min | 0.03 |
| Elution Pump Flow | mL/min | 0.5 |

Example 4

Figure 6:
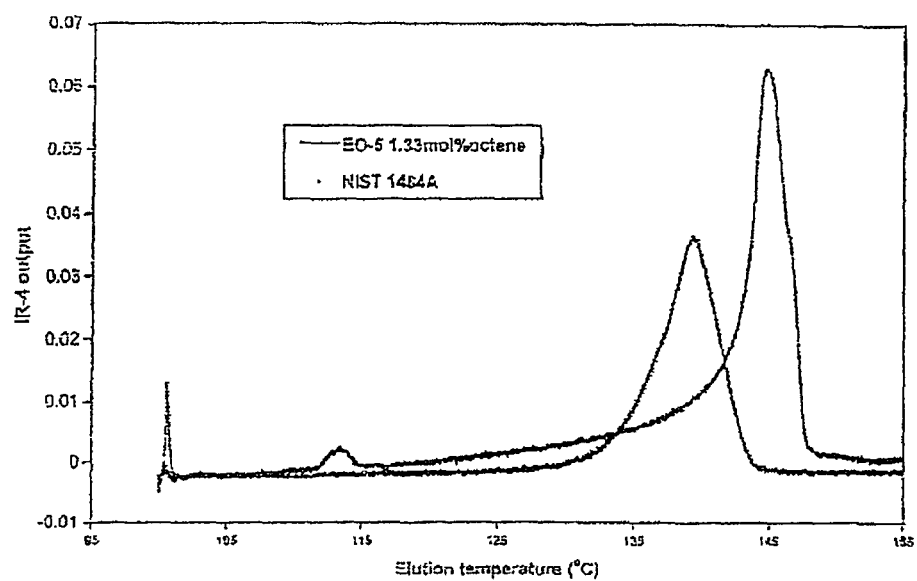
FIG. 6 is TGIC chromatograms of EO-5 and NIST polyethylene 1484A by using a column packed with a mixture of 33 wt % graphite and 67 wt % glass bead of 27 μm.
Figure 7:
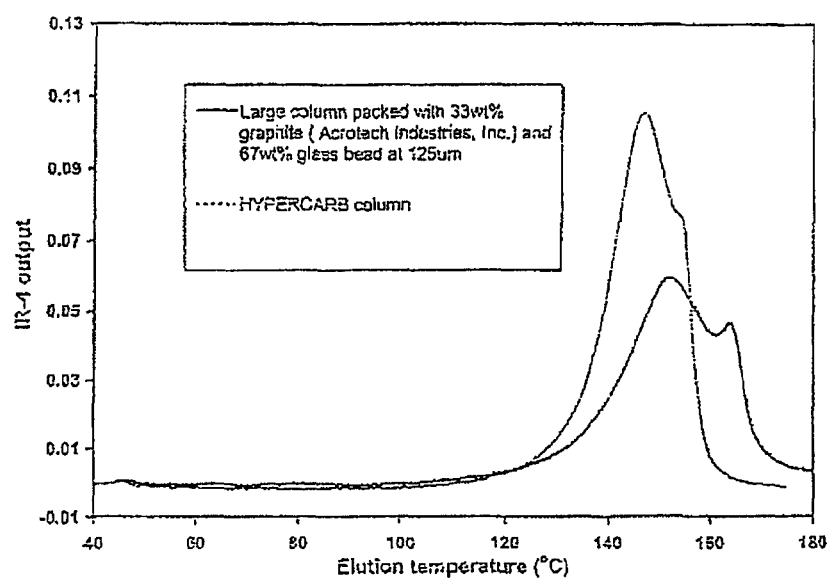
FIG. 7 is the TGIC chromatogram of EO-13 separated using a column packed with a mixture of 33 wt % graphite and 67 wt % glass bead of 125 μm, and using a HYPERCARB column.

Graphite purchased from Panef (a division of Acrotech Industries, Inc, Milwaukee, Wis., and sold under the name of "Graphite Lubricant") is used as a packing material. ODCB is used as the mobile phase. The graphite lubricant (33 wt %) is well mixed with 67 wt % of "27 µm glass spheres" (MO-SCI Specialty Products, LLC, Rolla Mich.). The mixture is used to pack a column made from a stainless tubing having an internal diameter of 0.085 inches, an external diameter of 0.125 inches, and a tubing length of 60 inches. The samples of EO-5 and NIST polyethylene standard of 1484a are analyzed by TGIC with this column. The detailed TGIC experimental parameters are listed in Table 3. The TGIC chromatograms of EO-5 and NIST 1484a are shown in FIG. 6. The NIST1484a elutes at a higher temperature than EO-5.

TABLE 3

TGIC experimental conditions for EO-5 to NIST PE 1484A with a column packed with a mixed graphite and glass bead of 27 µm.

| Dissolution Time at 160° C. | min | 120 |
|---|---|---|
| Loading loop volume | mL | 0.2 |
| Stabilization Temperature | ° C. | 150 |
| Stabilization Rate | ° C./min | 40 |
| Stabilization Time (Pre) | min | 2 |
| Stabilization Time (Post) | min | 2 |
| Crystallization Temperature | ° C. | 100 |

TABLE 3-continued

TGIC experimental conditions for EO-5 to NIST PE 1484A with a column packed with a mixed graphite and glass bead of 27 μm.

| | | |
|---|---|---|
| Crystallization Rate | ° C./min | 3 |
| Crystallization Time | min | 2 |
| SF Time | min | 2 |
| Elution Temperature | ° C. | 165 |
| Elution Rate | ° C./min | 0.5 |
| Crystallization Pump Flow | mL/min | 0.11 |
| Elution Pump Flow | mL/min | 0.5 |

Example 5

It has been discovered that using a long column in an inventive TGIC analysis is beneficial for resolution improvement, by using a small solvent flow during cooling process. It has also been discovered that a slow flow during cooling process of TGIC (the nomenclature of this process in CEF instrument was given as crystallization) allows a further separation of anchored chains (anchored to the stationary phase) from unanchored chains. Flow pushes the unanchored chains along the column. This benefit is demonstrated by using EO-13. EO-13 is made by an Z-N catalyst, and has a density of 0.920 g/cm$^3$ and melt index of 1.0 g/10 min. A column volume of "2.3 ml" is packed with a mixture of 33 wt % of graphite lubricant (A division of Acrotech Industries, Inc, Milwaukee, Wis.) and 67 wt % of 125 μm glass bead (MO-SCI Specialty Products, LLC, Rolla, Mich.). The column is a stainless tube having an internal diameter of 0.085 inches, an external diameter of 0.125 inches, and a length of 60 inches. ODCB is used as the mobile phase. Table 4 shows the TGIC experimental conditions for the column packed with this mixture of 33 wt % graphite and 67 wt % "125 um" glass bead, and for the HYPERCARB column (Thermo Scientific) with the column volume being measured as 0.7 ml. The respective chromatograms of EO-13, using these two columns, are shown in FIG. 6. As shown in FIG. 6, a better separation is achieved with the longer column, which, in turn, allows for the use of a higher flow rate (0.15 ml/min) during the cooling process, as compared to the slower flow rate for the "100 mm" commercially available HYPERCARB column (0.03 ml/min).

TABLE 4

TGIC experimental conditions for EO-13 analyzed with HYPERCARB column and the column packed with a mixed graphite and glass bead of 125 μm.

| TGIC experimental conditions | | For EO-13 with Mixed 33 wt % graphite and 67 wt % 125 mm glass bead | For EO-13 with HYPERCARB column |
|---|---|---|---|
| Dissolution Time at 160° C. | min | 120 | 120 |
| Loading loop volume | mL | 0.2 | 0.2 |
| Concentration | mg/ml | 2 | 2 |
| Stabilization Temperature | ° C. | 150 | 140 |
| Stabilization Rate | ° C./min | 40 | 40 |
| Stabilization Time (Pre) | min | 2 | 2 |
| Stabilization Time (Post) | min | 2 | 2 |
| Crystallization Temperature | ° C. | 40 | 40 |
| Crystallization Rate | ° C./min | 10 | 6 |
| Crystallization Time | min | 2 | 2 |
| SF Time | min | 2 | 2 |
| Elution Temperature | ° C. | 180 | 175 |
| Elution Rate | ° C./min | 3 | 3 |
| Crystallization Pump Flow | mL/min | 0.15 | 0.03 |
| Elution Pump Flow | mL/min | 0.4 | 0.5 |

Although the invention has been described in considerable detail in the preceding examples, this detail is for the purpose of illustration, and is not to be construed as a limitation on the invention, as described in the following claims.

The invention claimed is:

1. A method for one-dimensional chromatography of a polyolefin polymer, comprising introducing a solution of the polyolefin polymer into a liquid flowing through a liquid chromatography stationary phase, the liquid chromatography stationary phase comprising graphitic carbon, and wherein the polyolefin polymer emerging from the liquid chromatography stationary phase has a retention factor greater than zero, and
    wherein the solution introduced into the liquid chromatography stationary phase is subjected to a solvent gradient.

2. The method of claim 1, wherein the liquid chromatographic stationary phase further comprises at least one inert filler.

3. The method of claim 2, wherein the at least one inert filler is glass.

4. The method of claim 2, wherein the stationary phase comprises greater than, or equal to, 50 weight percent of the inert filler, based on the sum weight of the filler and graphitic carbon.

5. The method of claim 2, wherein the inert filler is in the form of spheres.

6. The method of claim 1, wherein the stationary phase is contained in a column that has an L/D ratio greater than 8, wherein L=column length, and D=external diameter of the column.

7. The method of claim 1, where the polyolefin polymer is a copolymer of ethylene and an alpha-olefin.

8. The method of claim 1, where the polyolefin polymer is a copolymer of propylene and an alpha-olefin.

9. A method for multi-dimensional chromatography of a polyolefin polymer, comprising introducing a solution of the polyolefin polymer into a liquid flowing through a first liquid chromatography stationary phase or a field flow fractionation device, and subsequently flowing the solution through a second liquid chromatography stationary phase, the second liquid chromatography stationary phase comprising graphitic carbon and at least one filler, and wherein the polyolefin polymer emerging from the liquid chromatography stationary phase has a retention factor greater than zero.

10. The method of claim 9, wherein the solution introduced into the first, or second, or both, liquid chromatography stationary phase(s), is/are subjected to a temperature gradient.

11. The method of claim 9, wherein the solution introduced into the first, or second, or both, liquid chromatography stationary phase(s), is/are subjected to a solvent gradient.

12. The method of claim 9, wherein the solution introduced into the first, or second, or both, liquid chromatography stationary phase(s), is/are subjected to both a temperature gradient and a solvent gradient.

13. An apparatus for polyolefin polymer chromatography, comprising a liquid chromatography stationary phase, the liquid chromatography stationary phase comprising graphitic carbon and at least one inert filler.

14. The apparatus of claim 13, further comprising a "temperature gradient device" and/or a "solvent gradient device."

* * * * *